United States Patent [19]
White et al.

[11] Patent Number: 5,992,236
[45] Date of Patent: Nov. 30, 1999

[54] ULTRASONIC INSPECTION METHOD

[75] Inventors: Dennis A. White, South Beloit; Gordon R. Voll, Durand; Richard L. Fearnside, South Beloit, all of Ill.

[73] Assignee: Beloit Technologies, Inc., Wilmington, Del.

[21] Appl. No.: 08/948,959

[22] Filed: Oct. 10, 1997

Related U.S. Application Data

[63] Continuation-in-part of application No. 08/690,763, Aug. 1, 1996, Pat. No. 5,681,996.

[51] Int. Cl.$^6$ ............................ G01N 29/06; G01N 29/10
[52] U.S. Cl. .................................. 73/622; 73/629; 73/634
[58] Field of Search ............................ 73/597, 598, 620, 73/622, 623, 624, 625, 628, 633, 634, 627, 629, 637, 641, 642, 644, 599, 600, 159

[56] References Cited

U.S. PATENT DOCUMENTS

| | | |
|---|---|---|
| 3,129,581 | 4/1964 | Bande . |
| 3,512,400 | 5/1970 | Lynnworth . |
| 3,918,296 | 11/1975 | Kitada . |
| 4,058,000 | 11/1977 | Ries et al. . |
| 4,164,150 | 8/1979 | Ries et al. . |
| 4,395,911 | 8/1983 | Macecek . |
| 4,398,421 | 8/1983 | White . |
| 4,472,975 | 9/1984 | Beck et al. . |
| 4,576,048 | 3/1986 | Glenn . |
| 4,577,505 | 3/1986 | Jestrich et al. . |
| 4,594,897 | 6/1986 | Bantz . |
| 4,658,649 | 4/1987 | Brook . |
| 4,679,437 | 7/1987 | Koike et al. . |
| 4,699,007 | 10/1987 | Kawashima et al. . |
| 4,760,737 | 8/1988 | Kupperman . |
| 5,161,412 | 11/1992 | John, Jr. et al. . |
| 5,267,481 | 12/1993 | Smith . |
| 5,383,365 | 1/1995 | Buttram . |
| 5,421,200 | 6/1995 | Casarcia et al. . |
| 5,492,012 | 2/1996 | Terhune . |
| 5,493,911 | 2/1996 | Hall et al. ................................. 73/597 |
| 5,497,662 | 3/1996 | Dykes . |
| 5,507,185 | 4/1996 | Pickens ..................................... 73/620 |

OTHER PUBLICATIONS

Nondestructive Testing Handbook (2d Edition, ©1991, American Society for Nondestructive Testing), vol. 7, Ultrasonic Testing, pp. 168, 254–257, 299–300, 400–401, 605–607, 864–865.

*Primary Examiner*—Hezron Williams
*Assistant Examiner*—Helen C. Kwok
*Attorney, Agent, or Firm*—Raymond W. Campbell; Gerald A. Mathews

[57] ABSTRACT

Radially spaced calibration holes are drilled parallel to the exterior surface of a cylindrical shell for a dryer roll. An ultrasonic transducer is mounted in a fixture filled with a coupling medium which allows for adjustment of the spacing and angle of the transducer which traverses the shell as it is rotated. The transducer produces a signal directed to the shell. A computer calculates the time the signal takes to travel from and return to the transducer and the depth of the shell from which the signal returns. A clear signal corresponding to holes up to one inch from the surface are found by adjusting the ultrasonic transmission angle. This angle is approximately 23 degrees from a normal to the casting surface. The calibrated transducer traverses the surface of the shell. The signals are gathered and stored to create data which may be used in maintaining the shell for the dryer roll.

30 Claims, 2 Drawing Sheets

ULTRASONIC INSPECTION METHOD

RELATED APPLICATION

This application is a continuation-in-part of U.S. patent application No. 08/690,763, filed Aug. 1, 1996 now U.S. Pat. No. 5,681,996.

FIELD OF THE INVENTION

The present invention relates to ultrasonic instruments for nondestructive testing of materials in general and for nondestructive testing of large cast cylinders in particular.

BACKGROUND OF THE INVENTION

In the manufacture of tissue paper and paper towel a web of paper fibers is formed and pressed against a Yankee dryer. After drying the web is scraped from the surface of the Yankee dryer, giving the web a creped texture which gives the paper it's soft absorptive characteristics. Because only a single dryer is used the Yankee dryer is normally large, typically from twelve to twenty-five feet in diameter. Moreover, the Yankee dryer is heated by steam at pressures of up to 160 psig. A Yankee dryer may be 400 inches long and may have a total weight of over 100 tons. Because of its large size and high operating pressure, a Yankee dryer typically has a cylinder wall thickness of over two inches. Yankee dryers are generally formed from cast iron; a material which has good release characteristics if the surface is properly ground. Thus the surface of a Yankee dryer requires periodic regrinding to maintain the proper surface finish.

A Yankee dryer is a pressure vessel and the safety precautions typically employed with any pressure vessel or boiler must be observed. In U.S. Pat. No. 4,398,421 an apparatus for measuring the thickness of a work piece which is useful for measuring the thickness of steam boiler walls is disclosed. Determining the wall thickness of a Yankee dryer is useful but it is also desirable to detect small voids within the thickness of the dryer wall.

Existing ultrasonic inspection systems have a limited capability for detecting small voids or finding voids near the surface of cast iron parts. Ultrasonic signals in cast iron are scattered and reflected from grain boundaries present in the cast iron. This characteristic of cast iron makes detecting small discontinuities very difficult. Even measurement of thickness in cast iron can be difficult to perform. One national study has found errors of over 40 percent in thickness measurements of cast iron with some conventional techniques. Ultrasonic transducers typically have an interface zone of up to one-half inch where subsurface discontinuities can not be detected.

X-ray methods are used for the inspection of Yankee dryer rolls. X-ray methods, however, require the use of radioactive sources which are cumbersome and dangerous. In practice, x-ray images are only made of limited portions of the Yankee dryer. Furthermore, x-ray imaging is not effective at detecting hair-line cracks because such cracks do not significantly reduce the density of the material. Hair-line cracks are, however, typically detectable by ultrasonics.

In the application No. 08/690,763 filed Aug. 1, 1996, which is incorporated herein by reference, a method of ultrasonic inspection was disclosed which is capable of detecting flaws in a Yankee dryer with a high signal-to-noise ratio.

In that application it was disclosed that if an ultrasonic signal is directed at a surface to be inspected at a particular angle, about ten percent of the signal will appear as Harris waves which propagate into the test plate at ninety degrees to the surface. The signal which propagates vertically is polarized, with the result that the signal detects flaws with greatly improved signal-to-noise ratio. The particular angle is between that angle where the ultrasonic signal is refracted so as to propagate parallel to the surface of the metal plate and that angle where the ultrasonic signal is reflected by the test plate. Employing shear waves, for an incident medium of water and a refracting medium of cast iron, the specific angle is approximately 33 degrees from the vertical. For steel the specific angle is approximately 31 degrees. For brass the angle is about 50 degrees.

This particular angle while detecting flaws, produced a signal without an apparent time of flight—meaning that the depth of the flaw could not be determined with the disclosed method. Methods of finding the depth of a flaw using ultrasonic energy can be difficult to calibrate. Traditional methods require a flat bottomed hole drilled from a surface opposite the surface from which the ultrasonic interrogation is conducted. A hole with a flat bottom is difficult to drill and difficult to precisely line up parallel to the interrogation surface.

What is needed is a method for performing complete inspection of a Yankee dryer for material defects which can determine the depth of any detected flaws.

SUMMARY OF THE INVENTION

The ultrasonic inspection method and apparatus of this invention is based on a calibration method and an empirically observed interrogation angle. Large dryer shells are made of cast iron because of its cost and good web release characteristics. The cylindrical shells are typically cast with the axis of the dryer oriented vertically. A portion of the cylindrical surface located at the bottom of the casting and referred to as a "dirt ring" is formed along with the cylindrical shell and separated from the dryer shell when the casting is fabricated into a dryer.

The cast cylinder together with the attached "dirt ring" is fabricated into a finished cylinder by mounting the cylinder on internal supports and positioning the cylinder in a lathe so that the surface of the roll can be machined. The surface of the casting together with the contiguous "dirt ring" is finished to a smooth cylindrical surface.

Calibration holes are drilled from the end of the cylindrical shell into the "dirt ring." The calibration holes are drilled parallel to the cylindrical shell surface. Multiple holes are drilled to form arrays of holes spaced about the circumference at varying depths from the cylinder surface. Arrays of holes of varying diameter are machined. Because the holes are not required to have flat bottoms the calibration holes are relatively easily machined at low cost.

The cutting tool which traverses the casting surface is replaced with an ultrasonic transducer mounted in a fixture which provides a coupling media between the transducer and the surface of the casting. The fixture provides for adjustability of the spacing between the transducer and the surface. The fixture also provides for varying the angle of the transducer with respect to the surface.

The ultrasonic transducer is then traversed over the "dirt ring" which contains the calibration holes by rotating the casting past the fixture and transducer positioned therein. The transducer produces pulses of high frequency sound which travel into the casting from the outwardly facing cylindrical surface. The transducer receives signals reflected from discontinuities in the thickness of the cylinder or sound path in the cylinder as the ultrasonic energy penetrate the casting. A computer or other signal processing device calculates the time the signal takes to travel from the transducer and return to the transducer. From this calculation the depth from which the signal is returned is determined. Alternatively, the return signal is divided into separate depth ranges depending on whether the return signal falls within a particular time gate.

It has been found empirically that a clear signal corresponding to calibration holes having depths varying from immediately adjacent to the surface to well over one inch, can be found by adjusting the angle at which the ultrasonic energy is transmitted towards the cylindrical surface. This angle tends to be slightly smaller than the angle disclosed as optimum in the application No. 08/690,763 filed Aug. 1, 1996. The angle is readily determined by trial and error and for cast iron appears to be approximately 23 degrees from a normal to the casting surface.

By traversing the "dirt ring" which has holes of known sizes and depths it is possible to calibrate the signal-receiving circuitry in a sensor, which is part of the transducer, both by adjusting the sensor for maximum sensitivity and correlating the data received from the sensor with known discontinuities in the casting. The transducer then traverses over the entire surface of the casting and the data is stored for analysis and future use in maintaining and repairing the dryer roll formed from the casting.

After inspection is complete, the "dirt ring" is removed from the rest of the casting and the surface of the casting is given a final machining operation.

It is a feature of the present invention to provide an inspection method for a cast dryer shell which can reliably detect discontinuities and their locations within the casting.

It is a further feature of the present invention to provide a fixture for mounting an ultrasonic transducer which can adjustability position the transducer with respect to a dryer surface.

It is another feature of the present invention to provide a data record which can be supplied with a Yankee dryer to aid in the maintenance and repair of the dryer.

Further objects, features and advantages of the invention will be apparent from the following detailed description when taken in conjunction with the accompanying drawings.

DESCRIPTION OF THE PREFERRED EMBODIMENT

Figure 1:
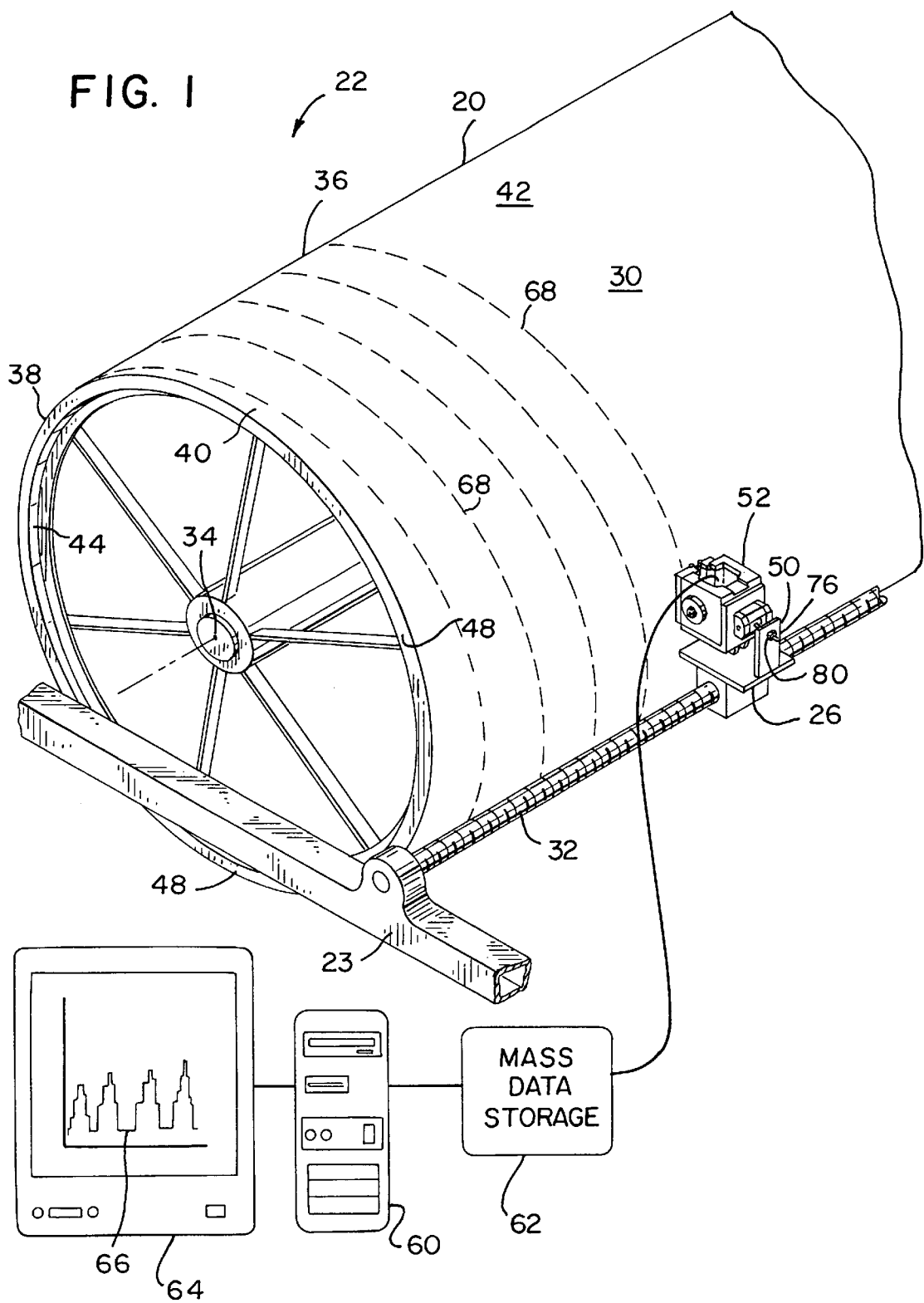
FIG. 1 is an isometric view of a dryer roll casting being inspected with ultrasonic energy and the results being recorded.
Figure 2:
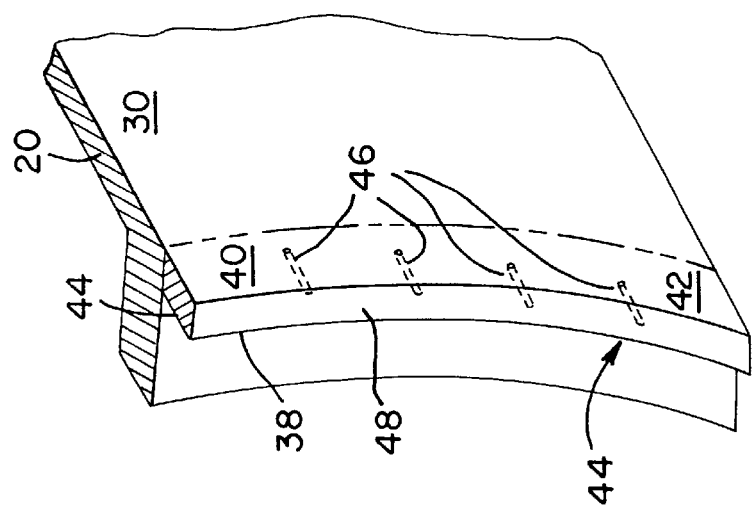
FIG. 2 is an isometric view of a portion of the dryer roll casting of FIG. 1 showing test holes machined parallel to the surface of the dryer.
Figure 3:
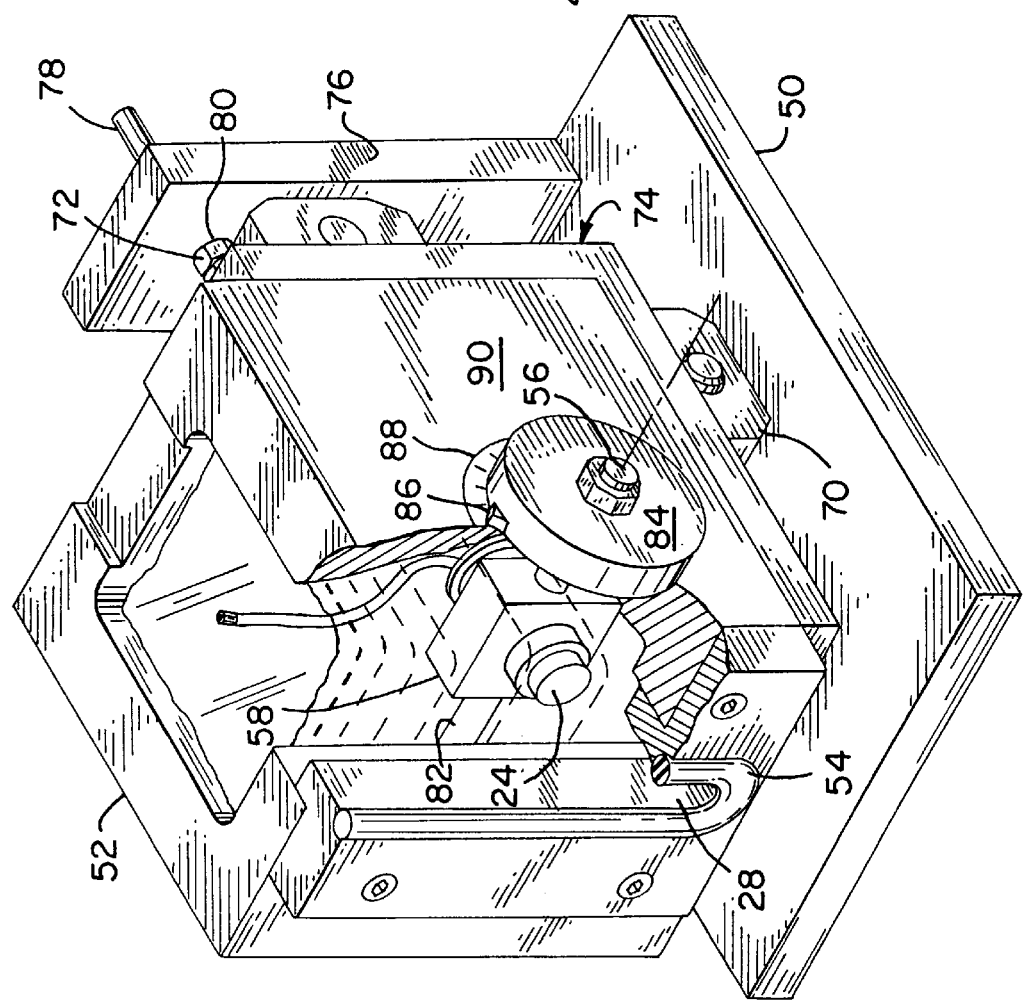
FIG. 3 is an isometric view partly cutaway of a fixture for adjustably positioning and coupling an ultrasonic transducer to the surface of the dryer roll of FIG. 1.

Referring more particularly to FIGS. 1–3, wherein like numbers refer to similar parts, a Yankee dryer casting 20 is shown mounted on a machining station 22. Yankee dryers are used to dry a tissue paper web. A wet tissue web is pressed onto the surface of a steam heated dryer roll which is typically twelve to twenty-five feet in diameter. The web is brought into intimate contact with the dryer surface, and often hot air is blown onto the surface of the web as it is transported by the Yankee dryer. A doctor blade scrapes the tissue web from the surface of the Yankee dryer once the web is dry, removing the web and at the same time imparting a crepe to the web which improves its absorbency and gives the web a soft surface texture.

The surface release characteristics are critical to the proper function of a Yankee dryer. Cast iron, preferably class 60 cast iron, is used to achieve the required surface characteristics. A Yankee dryer is typically heated internally by steam. Thus the dryer as it is used is a pressure vessel which is typically pressurized to about 160 psig. The size and required high uniformity of the casting results in a very expensive unit.

Periodically over the life of a Yankee dryer, the surface must be reground as it becomes worn. Grinding the surface can expose hidden defects in the dryer surface which must then be repaired. Because the Yankee dryer is a pressure vessel the presence of flaws in the dryer shell is always a concern.

Inspection of the material making up the cylindrical wall of a Yankee dryer is highly desirable both to preserve the overall integrity of the pressure vessel and also to have the ability to predict when surface flaws will be uncovered as the dryer roll surface is ground down with use.

Conventional ultrasonic techniques are not very effective with cast iron because of the many grain boundaries within the material. Typically the dryers are inspected by bouncing ultrasonic energy off the inside surface of the dryer shell and monitoring the attenuation of an ultrasonic signal as it twice passes through the thickness of the shell. This provides limited information about the presence of material defects. An ASTM standard for this type of measurement has been developed.

The method of this invention employs an ultrasonic transducer 24, shown in FIG. 3, which is mounted in a fixture 26. The fixture 26 is adjustable to position a U-shaped aperture 28 against the surface 30 of the casting 20. The fixture 26 is mounted to a lead screw 32 and can be moved parallel to the surface 30 of the Yankee dryer shell 36 in a direction parallel to the axis 34 of the dryer cylinder casting 20.

The casting 20 consists of the cylindrical shell 36 which will form the shell of a Yankee dryer, and a portion 38 of the casting 20 which is referred to as a "dirt ring". The "dirt ring" 38 is formed with the Yankee cylindrical shell 36 and has a surface 40 which is co-extensive with the surface 42 of the Yankee cylindrical shell 36. The "dirt ring" also has a thickness which is comparable to the thickness of the Yankee shell 36. The "dirt ring" 38 is machined away from the Yankee shell 36 to form the finished dryer.

Because the "dirt ring" 38 does not form part of the finished dryer it can be used to calibrate a test procedure. In the past, calibration holes were drilled from the back side 44 of the dirt ring. These holes required a flat bottom which was tangent to the surface from which the ultrasonic inspection is conducted. Machining a flat bottomed hole is a difficult and expensive procedure. A hole which presents a curved surface as viewed from the exterior cylindrical surface produces extensive scattering of an ultrasonic beam and so is regarded as an impractical approach.

The improved inspection process of this invention utilizes holes 46 which are drilled from the edge 48 of the "dirt ring" 38 parallel to the axis 34 of the dryer and spaced a known distance beneath the "dirt ring" surface 40. The holes 46 present curved surfaces which would be expected to scatter an ultrasonic signal. However it has been found that proper positioning of a transducer with respect to the surface 40 results in a clearly identifiable signal which can be correlated with the holes 46. The holes 46 are machined in groups with uniform spacing between holes. Typical hole sizes corresponding to minimum flaw size is one millimeter in diameter. Other holes having diameters of three, five, and ten millimeters are also machined in the "dirt ring" 38.

The transducer 24 is positioned within a tank 52 with the U-shaped aperture 28 engaged against the "dirt ring" surface 40. The fixture has a mounting bracket 50 which allows the tank 52 containing the transducer 24 to position the aperture 28 against the "dirt ring" surface 40. A compressible gasket 54 surrounds the aperture 28 sealing the aperture to the casting 20 surface. The tank 52 is filled with water or oil, preferably an organic oil such as castor oil. The entire casting 20 including the "dirt ring" 38 is caused to rotate on the machine frame 23. Rotation causes the holes 46 to pass in front of the aperture 28. The transducer 24 is energized and sends periodic pulses of ultrasonic energy towards the surface 40 of the "dirt ring" 38.

By trial and error the transducer 24 is adjusted until a strong signal is detected by the sensor in the transducer from the holes 46 as they pass beneath the transducer 24. The fixture 26 is designed to allow rotation of the transducer about an axis 56 parallel to the axis 34 of the casting 20. Rotation about the axis 56 adjusts the angle of incidence between the ultrasonic beam and a line normal to the surface 30 of the casting 20. The transducer 24 is slidably mounted in a block 58 which allows the transducer 24 to be moved towards and away from the surface 30 of the casting 20. The transducer 24 is thus adjustably positioned over the surface 40 of the "dirt ring" 38. It has been found, in conjunction with a tank 52 filled with water, that at an angle of about 23–28 degrees, with a transducer spacing from the surface 40 of about two inches to about two and one-quarter inches a clear signal is returned from the test holes which has a time of flight which is related to the depth of the test hole. By monitoring the signal received as the calibration holes 46 are moved beneath the transducer 24 the optimal spacing and angle for detecting the holes is readily determined. Because the location of the calibration holes beneath the surface 40 of the "dirt ring" 38 is known, a depth of a hole can be correlated with the time of flight of the ultrasonic signal.

Correlation of flaw depth with time of flight of the signal can be performed by time gating the return signal. Time gating the signal divides the return signal into various portions which have times of flight between two selected times. Typically a single time gate may be used to simplify the return data. The "dirt ring" 38 and the calibration holes 46 are scanned with a single time gate corresponding to the first 1/10th inch of the casting 20 thickness beneath the surface 40. Other useful time gates might correlate with a band of material making up layers of the casting of 2/10ths to 5/10ths of an inch thick, but may even be used up to the full thickness of the casting. A dryer roll, particularly a Yankee dryer roll, may be as thick as four inches and the technique can be used to detect flaws from the thickness of the dryer by proper use of time gates which are correlated with calibration holes.

A computer 60 or other signal processing device calculates the time the signal takes to travel from the transducer and return to the transducer. The return signal can also be correlated with its time of flight on a point-by-point relationship within the speed and data rate capabilities of the computer 60 and a data storage system 62. A data record may thus be assembled containing a multiplicity of individual records, each individual record uniquely correlated with a location on the cylindrical surface, and each individual record containing at least one value corresponding to a recorded value obtained by interrogating the cast cylindrical shell from the surface with ultrasonic energy and recording a value related to the time of flight of any signal reflected to the surface at each location on the cylindrical surface.

Once the ultrasonic transducer 24 has been calibrated the fixture 26 containing the transducer 24 is scanned over the entire surface 42 of the casting 20. Scanning speeds of as high as between six inches and twenty-four inches per second have been found to be practical. The data collected is stored in the data storage system 62 and can then be viewed on a monitor 64. The monitor can display a map of the casting 20 with different layers corresponding to the depth at which flaws are detected. The monitor display 66 shown in FIG. 1 shows a number of calibration holes at varying depths beneath the surface 40 of the "dirt ring" 38.

For a casting having a diameter of twenty-five feet, and a spiral pattern 68, where successive scans are one-eighth inch apart, the scanning process will take about one to four hours per foot of casting length.

The fixture 26, as shown in FIG. 1, is mounted to the lead screw 32. The fixture can be mounted by a compound tool rest (not shown). The tank 52 is mounted to the bracket 50 by a pivot mount 70 positioned beneath the tank 52 which allows the gasket 54 to be tilted forward towards the casting surface 30. A pivoting extension mechanism 72 connects the back side 74 of the tank 52 to an upstanding flange 76. A threaded rod 78 passes through the flange 76 and an opposed nuts 80 locks the rod 78 in position and thus locks the tilt angle of the tank 52.

The transducer 24 is slidably mounted within the tank 52 in the block 58. The block 58 in turn is rigidly mounted to a threaded rod 82 which rotates about the axis 56. A dial 84 with an indicator 86 is mounted to the rod 82. Rotation of the dial 84 and the connected rod controls the position of the transducer 24 with respect to a line normal to the surface 30 of the casting. A scale 88 mounted on the side 90 of the tank 52 allows the angle of the transducer to be determined. Locking nuts (not shown) on the threaded portion (not shown) of the shaft opposite the dial 84 can be used to lock the shaft in position.

It should be understood that the transducer may be mounted to any appropriate mechanism which has at least two degrees of freedom including one degree of translation away from the casting surface, and one degree of rotation to vary the angle of the transducer with respect to a line normal to the casting surface towards which the ultrasonic transducer 24 faces. The rotation of the transducer will preferably be about an axis parallel to the axis 34 of the casting 20.

It should be understood that dual ultrasonic transducers could be used and one of the ultrasonic signals could be used to gather the whole thickness attenuation data by recording back face reflectivity as required by ASTM testing standards. Thus the flaw detection and depth data could be gathered with data required to meet the ASTM requirements.

Ultrasonic energy over a wide range has been used for ultrasonic testing upon solid materials and ultrasonic frequencies of 1 to 10 MHZ in particular have been found to be effective.

It should be understood that the data gathered in the mass storage system 62 can typically be 20 megabytes or more and can be supplied with the finished dryer constructed from the casting 20. The data could be supplied on high density storage media such as a DVD (digital versatile disk) or could be made available to the purchaser over the Internet or similar data network. The data also might be supplied as part of a service contract with the data being made available together with other services to maintain and repair a dryer over its useful life.

After the casting 20 is inspected an additional one twentieth of an inch of material is removed from the surface, the dirt ring is removed and the dryer is completed by the provision of ends or heads together with necessary internal plumbing.

It is understood that the invention is not limited to the particular construction and arrangement of parts herein illustrated and described, but embraces such modified forms thereof as come within the scope of the following claims.

We claim:

1. A method of inspecting a cast shell of a dryer with ultrasound comprising the steps of:
   mounting a cast shell of a dryer for rotation about an axis of symmetry, the shell having a surface;
   drilling at least one calibration hole parallel to the surface of the shell;
   mounting an ultrasonic transducer adjacent to the surface of the shell overlying the calibration hole and providing an ultrasonic coupling medium between the transducer and the surface of the shell;
   producing pulses of high frequency sound from the ultrasonic transducer;
   rotating the shell about the axis so the surface overlying the calibration hole passes beneath the transducer;
   adjusting an angle of the transducer and a distance of the transducer from the surface until a reflected signal is detected from the calibration hole; and
   scanning an entire surface of the dryer shell with the ultrasonic transducer positioned as determined in the step of mounting the ultrasonic transducer;
   receiving signals in the ultrasonic transducer reflected from discontinuities in the thickness of the shell or sound path in the shell.

2. The method of claim 1 wherein the angle between the transducer and a normal to the surface of the shell is about 23 degrees.

3. The method of claim 1 wherein the shell is constructed of cast iron and wherein a portion of the casting which is later discarded is used to contain the calibration hole.

4. The method of claim 1 wherein a multiplicity of holes of varying sizes and depths are drilled parallel to the shell surface so that flaws of various sizes and depths can be simulated and the ultrasonic transducer calibrated to detect the flaws.

5. The method of claim 1 further comprising the step of storing the signals collected from the shell for later processing.

6. The method of claim 1 wherein the step of receiving signals is effected by a transducer having a sensor placed in a tank of coupling fluid which is sealed to the surface of the shell, and wherein the transducer with the sensor can be moved within the tank to adjust the angle and distance between the transducer and the surface of the dryer shell.

7. The method of claim 6 wherein the sensor is mounted to provide at least two degrees of freedom, including a degree of translation towards and away from the shell surface, and a degree of rotation about an axis parallel to the axis of symmetry of the cast dryer shell.

8. The method of claim 6 wherein an organic oil is used as the coupling fluid.

9. The method of claim 1 wherein two or more holes having a diameter of about one millimeter are drilled at intervals of between about $2/10$ and $5/10$ inches are used.

10. The method of claim 1 wherein two or more holes having a diameter of about one millimeter are drilled at intervals of between about $5/10$ inches and the thickness of the shell.

11. The method of claim 1 wherein information from the transducer is processed to detect discontinuities and recorded, and later recalled and displayed on a video monitor.

12. The method of claim 1 wherein the shell is for a dryer roll of a Yankee type having a diameter between 12 and 25 feet.

13. The method of claim 1 wherein the signal received from the transducer is time gated so that any return signal falls in a bin of time corresponding to a particular depth range beneath the surface of the dryer roll.

14. The method of claim 1 wherein the signal received from the transducer is time gated so that any return signal falls in a bin of time corresponding to a particular sound path range beneath the surface of the dryer roll.

15. The method of claim 1 wherein the surface is scanned at a rate of between six and twenty-four inches per second.

16. A method of inspecting a shell dryer with ultrasound comprising the steps of:
   mounting a shell of a dryer for rotation about an axis of symmetry, the shell having an outer surface;
   drilling at least one calibration hole parallel to the axis of symmetry spaced inwardly from the outer surface of the shell;
   mounting an ultrasonic transducer adjacent to the outer surface of the shell overlying the calibration hole, and providing an ultrasonic coupling medium between the transducer and the surface of the shell;
   producing a signal from the ultrasonic transducer, which signal is for calibrating the transducer;
   creating relative motion between the shell outer surface and the ultrasonic transducer so the surface overlying the calibration hole passes beneath the transducer to provide a signal which is an indication of any discontinuities in the shell;
   adjusting an angle of the transducer and a distance of the transducer from the outer surface until a reflected signal from the transducer is detected from the calibration hole by a sensor in the transducer; and
   scanning an entire surface of the shell with the ultrasonic transducer positioned as determined in the calibration step.

17. The method of claim 16 wherein the angle between the transducer and a normal to the surface of the shell is about 23 degrees.

18. The method of claim 16 wherein the dryer is constructed of cast iron and wherein a portion of the casting which is later discarded is used to contain the calibration holes.

19. The method of claim 16 wherein a multiplicity of holes of varying sizes and depths are drilled parallel to the outer surface so that flaws of various sizes and depths can be simulated and the sensor calibrated to detect the flaws.

20. The method of claim 16 further comprising the step of storing the signals collected from the shell by the ultrasonic transducer for later processing.

21. The method of claim 16 wherein the transducer with the sensor is placed in a tank of coupling fluid which is sealed to the surface of the shell and wherein the sensor can be moved within the tank to adjust the angle and distance between the transducer and the surface of the dryer shell.

22. The method of claim 21 wherein the sensor is mounted to provide two degrees of freedom, including a degree of translation towards and away from the shell surface, and a degree of rotation about an axis parallel to the axis of symmetry of the dryer shell.

23. The method of claim 21 wherein an organic oil is used as the coupling fluid.

24. The method of claim 16 wherein two or more holes having a diameter of about one millimeter are drilled at intervals of between about $\frac{2}{10}$ and $\frac{5}{10}$ inches are used.

25. The method of claim 16 wherein two or more holes having a diameter of about one millimeter are drilled at intervals of between about $\frac{5}{10}$ inches and the thickness of the shell.

26. The method of claim 16 wherein information from the transducer is processed to detect discontinuities and recorded, and later recalled and displayed on a video monitor.

27. The method of claim 16 wherein the shell is for a dryer roll of a Yankee type having a diameter between 12 and 25 feet.

28. The method of claim 16 wherein the signal received from the transducer is time gated so that any return signal falls in a bin of time corresponding to a particular depth range beneath the surface of the shell.

29. The method of claim 16 wherein the signal received from the transducer is time gated so that any return signal falls in a bin of time corresponding to a particular sound path range beneath the surface of the shell.

30. The method of claim 16 wherein the surface is scanned at a rate of between six and twenty-four inches per second.

* * * * *